US007277522B2

(12) United States Patent
Bruder et al.

(10) Patent No.: US 7,277,522 B2
(45) Date of Patent: Oct. 2, 2007

(54) METHOD FOR FOCUS ADJUSTMENT IN A CT APPARATUS

(75) Inventors: Herbert Bruder, Höchstadt (DE); Martin Petersilka, Adelsdorf (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/482,263

(22) Filed: Jul. 6, 2006

(65) Prior Publication Data
US 2007/0023713 A1  Feb. 1, 2007

(30) Foreign Application Priority Data
Jul. 7, 2005 (DE) .................. 10 2005 031 893

(51) Int. Cl.
*G01N 23/00* (2006.01)

(52) U.S. Cl. ........................................ 378/14; 378/205
(58) Field of Classification Search .................. 378/19, 378/4, 8, 20, 16, 205, 207
See application file for complete search history.

(56) References Cited

U.S. PATENT DOCUMENTS 5,625,661 A * 4/1997 Oikawa ........................ 378/15
6,256,369 B1 * 7/2001 Lai ............................. 378/14

* cited by examiner

*Primary Examiner*—Hoon Song
(74) *Attorney, Agent, or Firm*—Schiff Hardin LLP

(57) ABSTRACT

In a method for non-iterative focus adjustment in a CT apparatus the position of the center ray with regard to the movement direction of the focus and the correct phase between the detector sampling frequency and the focus springing frequency are calculated with a minimal number of sinogram acquisitions and is adjusted without iterative steps, corresponding to predetermined values.

14 Claims, 6 Drawing Sheets

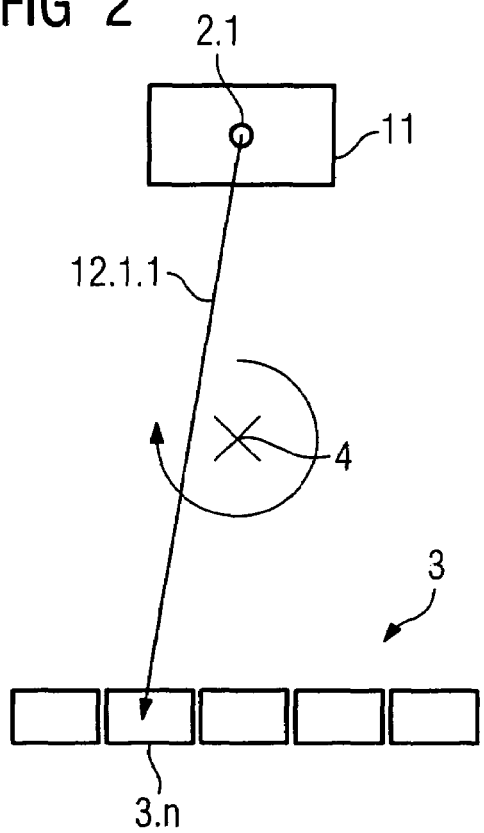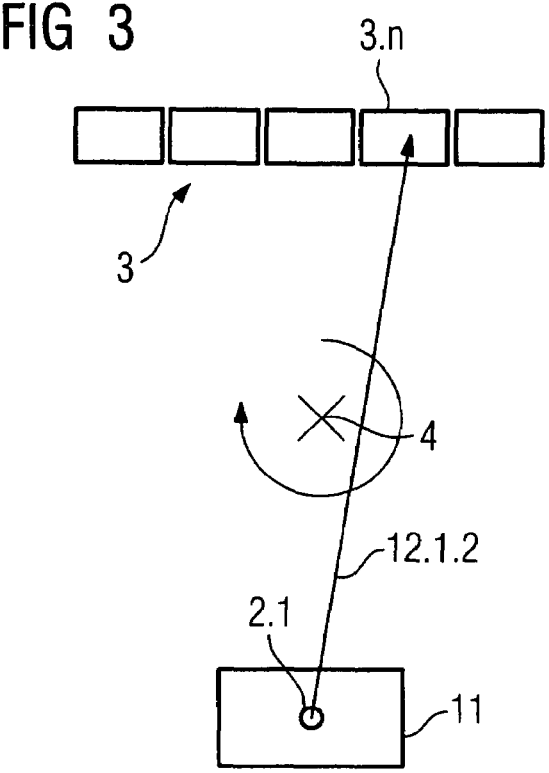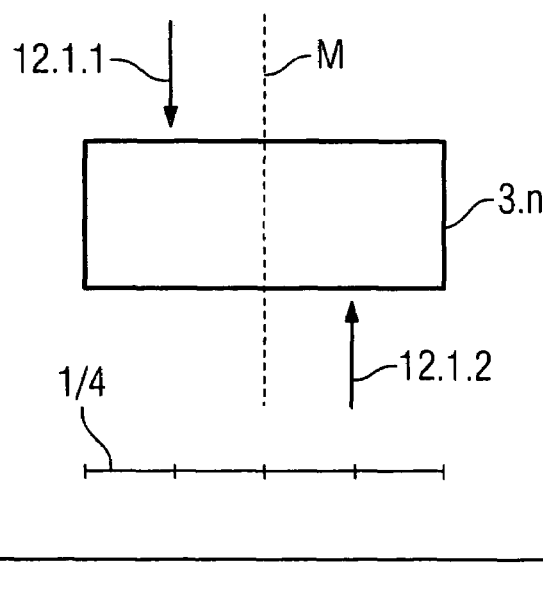

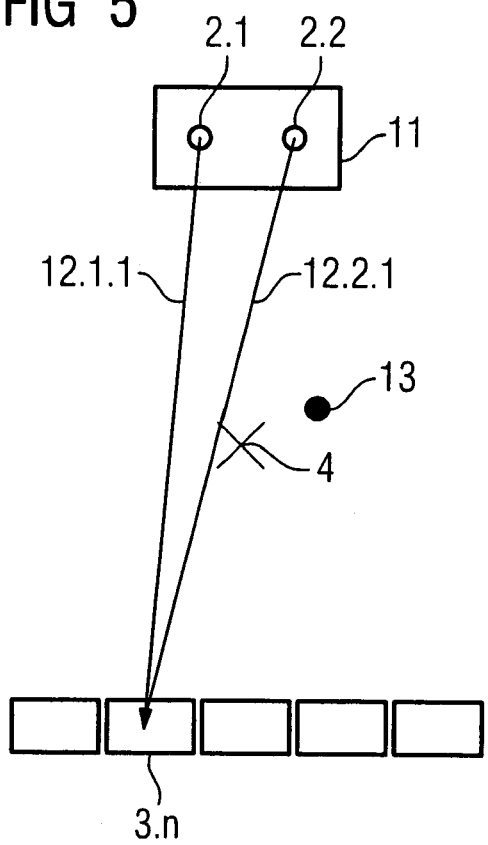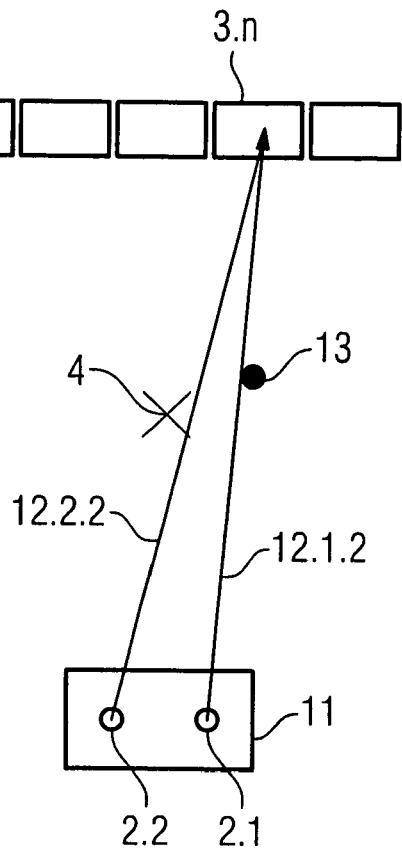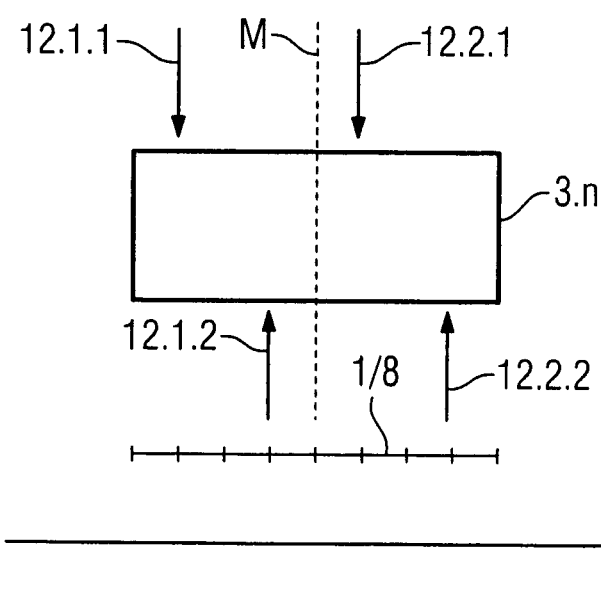

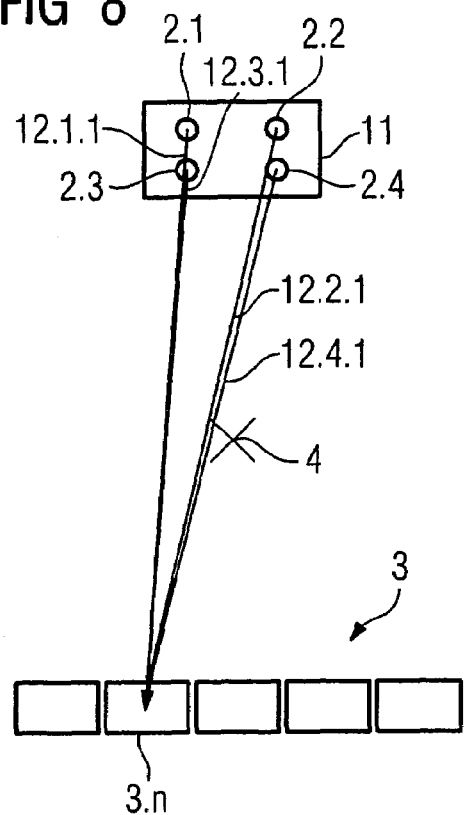
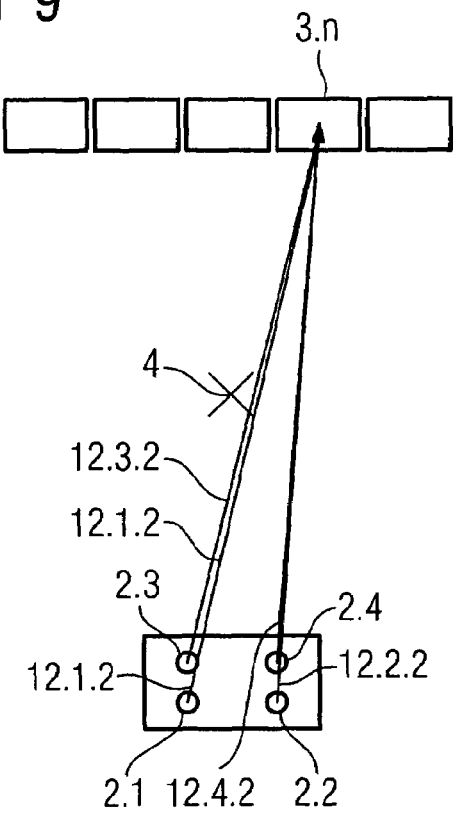
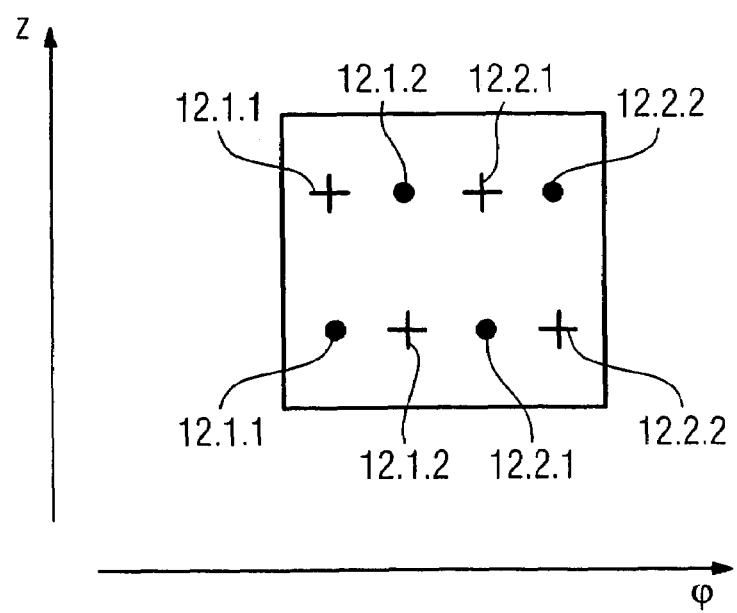

METHOD FOR FOCUS ADJUSTMENT IN A CT APPARATUS

BACKGROUND OF THE INVENTION

1. Field of the Invention

The present invention concerns a method for focus adjustment in a CT (computed tomography) apparatus of the type having at least one x-ray tube with a springing focus, that x-ray tube rotating around a system axis, and a multi-line detector with a plurality of detector elements, is situated opposite the x-ray tube.

2. Description of the Prior Art

CT apparatus of the above type is known wherein the focus on the anode changes position in one dimension or in two dimensions with a specific focus jump frequency. The output signals of the detector elements of the detector are integrated with a specific detector sampling frequency. The focus jump frequency is equal to the detector sampling frequency; and the jumped-to focus positions and the phase shift are set between the focus jump frequency and the detector sampling frequency.

It is generally known that a springing focus arrangement can be used to improve the spatial resolution of a CT apparatus. Using a magnetic deflection system in the x-ray tube, the radiation-generating electron beam is influenced such that a plurality of positions on the anode can be jumped to with a specific springing focus frequency, and thereby each detector element can be irradiated from different directions and exposed multiple times in a projection. The sampling of the detector signals ensues with a frequency that results from the plurality of the projections per rotation of the gantry, the rotation speed and the plurality of the different springing focus positions. If the sampling ensues with suitably shifted focal point, the effective sampling rate can be multiplied and the resolution and quality of the CT examination can be improved.

The focus deflection can be implemented both in the axial direction (Z-direction=system axis direction) and in the transaxial direction (φ-direction=circumferential direction=azimuthal direction) or in combinations of both directions. In each case it is necessary to determine the phase relation between the deflection movement of the focus (focus springing frequency) and the frequency of the data acquisition (detector sampling frequency), the deflection difference in the springing focus positions and the absolute focus position on the anode (focus offset).

For example, by correct selection of the deflection of the springing focus (focus offset) in the azimuthal direction two positions are achieved (known as focus alignment in the rotation center of the gantry) as well as a quadruple sampling of the detector pixels in the rotation center in connection with an azimuthal springing focus and a known ¼ offset of the detector elements. A transfer frequency of the imaging system (focus/detector system) that is four times higher is thus enabled.

For this purpose it is necessary to carefully match the alignment of the springing focus positions and the phase shift between the focus springing frequency and the detector sampling frequency. In principle, these quantities can be determined from CT scans with orbital sampling and a suitable phantom in a springing focus operation. An eccentrically positioned, strongly attenuating small sphere or (if the springing focus jumps only in the azimuthal direction) a small cylinder is suitable as a phantom. This matching is conventionally achieved by iterative approximation of the optimal deflection of the focus and the optimal phase with multiple measurements and intervening evaluations.

Such iterative methods are very time-consuming and costly and there is need to simplify and shorten such procedures.

SUMMARY OF THE INVENTION

An object of the present invention is to provide a method for focus adjustment in a CT apparatus with a springing focus that operates sufficiently well with a minimum of measurement and time expenditure.

The invention is based on the recognition that, with the acquisition of a low plurality of sinograms of a phantom with different parameters with regard to the position of the focus, and the phase between the detector sampling frequency and the focus springing frequency, it is possible to determine the correct correction values for the jumped-to focus positions and the phase adjustment directly, and without an iterative procedure.

Based on this recognition, the above object is achieved by a method for non-iterative focus adjustment in a CT apparatus that has at least one x-ray tube with a springing focus, the x-ray tube rotating around a system axis, and a multi-line detector with a plurality of detector elements that is situated opposite the at least one x-ray tube, wherein the focus changes position on the anode in one dimension or in two dimensions with a specific focus springing frequency; the output signals of the detector elements of the detector being integrated with a specific detector sampling frequency, and the focus springing frequency being equal to the detector sampling frequency, and the position of the center ray being calculated with regard to the movement direction of the focus and the phase between the detector sampling frequency, and the focus springing frequency is determined and adjusted by predetermined steps. At least three sinograms of a spherical or cylindrical absorber are acquired at positions of the focus in one dimension that alternate during the acquisition, or at least five sinograms of a spherical or cylindrical absorber are acquired at positions of the focus in two dimensions that alternate during the acquisition. The sinograms are acquired with different parameters with regard to the position of the focus and the phase between the detector sampling frequency and the focus springing frequency, and furthermore from the acquired sinograms.

Iterative steps thus are not needed with and the correct or optimal phase can be set. The specified minimum values of measurement sinograms represent the mathematically necessary minimum values for an exact calculation, in which linear relationships must exist in the range of the measurement values. Although the invention is implemented without an iterative procedure when a larger plurality of measurements is conducted an improvement in the precision is achieved. This means that all measurements are conducted with the same conditions, thus the same focus offset, and no adjustment of the focus offset and no approximation to a selected phase ensues between the measurements.

The measurement results to be supplemented by the focus deflections that are necessary for determination of the desired focus positions and phase, being determined by scaling with the focus deflection and interpolation.

The following formula can be used for scaling the focus deflection in one dimension:

$$(\Theta_1 - \Theta_2)(\tau_i, \rho_k) = (\Theta_1 - \Theta_2)(\tau_i, \rho_i) \cdot \frac{\rho_k}{\rho_i}, \text{ with } 1 \le k, i \le N$$

wherein $\Theta_1$ and $\Theta_2$ are the alignments of the first and second focus positions, $\tau_i$ is the phase between the detector sampling frequency $f_D$ and the focus springing frequency $f_F$, $\rho_k$ is a value proportional to the focus deflection (such as a deflection current), and the alignments $\Theta_1$ and $\Theta_2$ are calculated from the sinograms of the respective focus positions according to $$\int_0^{2\pi} \beta(\alpha) d\alpha = 2\pi\Theta,$$

wherein $\beta(\alpha)$ corresponds to the emphasis line of the absorption of the absorber in the sinogram and $\alpha$ corresponds to the projection angle.

An equidistant oversampling of the detector channels can be achieved by the interaction between a set detector offset and the set focus positions.

Furthermore, the focus positions and the phase between the detector sampling frequency and the focus springing frequency can be determined by interpolation using a trapezoidal time function.

The invention is non-iterative for determination of phase, amplitude and offsets of the dynamic focus deflection. Thus the focus alignment adjustment can be significantly accelerated. By suitable establishment of different values for the phase, deflection amplitude and focus offset, the optimal values can be calculated from sequential measurements with a suitable phantom.

For explanation of the invention, the scanning of a subject with a CT apparatus with springing focus is described. Initially only a springing focus with two different focus positions in the azimuthal direction is described, and subsequently an expansion of the springing focus in the system axis direction is described.

DESCRIPTION OF THE DRAWINGS

FIG. 2 schematically shows a normal focus of a CT apparatus with the detector situated opposite thereto in the vertical position with ⅛ offset.

FIG. 3 shows the components of FIG. 2 after a rotation by 180° around the system axis.

FIG. 4 shows section of a virtual detector element in the rotation center with spatial distribution of the x-rays from the opposite projection directions.

FIG. 5 schematically shows a springing focus with two focus positions of a CT apparatus with the detector opposite thereto in the vertical position with ¼ offset.

FIG. 6 shows the components of FIG. 5 after a rotation by 180° around the system axis.

FIG. 7 shows a section of a virtual detector element in the rotation center with spatial distribution of the x-rays from the opposite projection directions and emanating from two different focus positions in the azimuthal direction.

FIG. 8 schematically shows a springing focus with four focus positions of a CT apparatus with the detector opposite thereto in the vertical position with ¼ offset.

FIG. 9 shows the components of FIG. 8 after a rotation by 180° around the system axis.

FIG. 10 shows a section of a virtual detector element in the rotation center with spatial distribution of the x-rays from the opposite projection directions and emanating from two different focus positions each in the azimuthal direction and in the z-direction.

DESCRIPTION OF THE PREFERRED EMBODIMENTS

Figure 1:
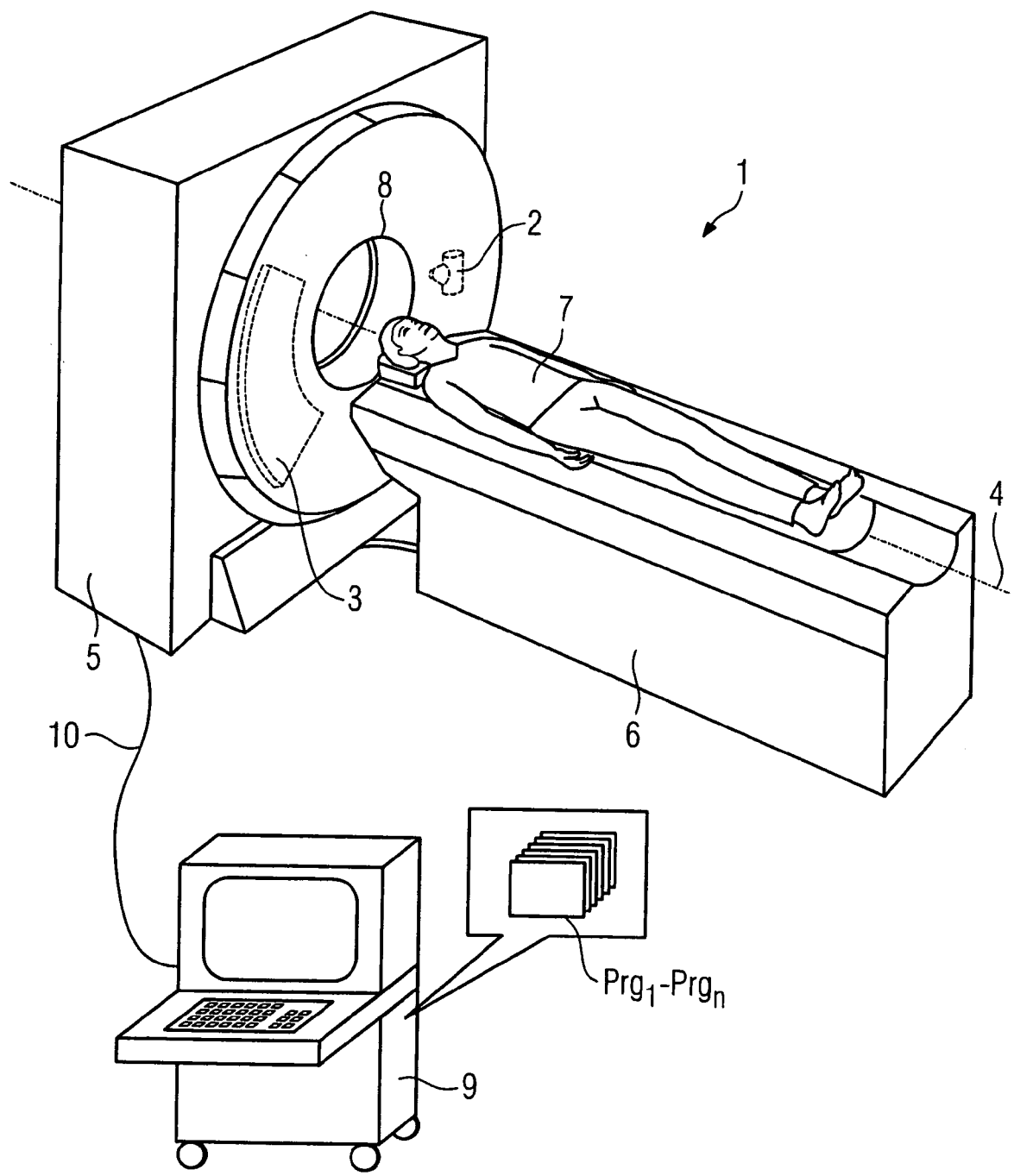
FIG. 1 is an overview of a CT apparatus.

FIG. 1 shows an exemplary computed tomography apparatus (CT) with which the inventive method can be implemented. The CT 1 has an x-ray tube 2 (mounted on a gantry (not shown in detail) in a housing 5) in which various focus positions can be controlled (activated) in the direction of the z-axis 4 and/or in the ϕ-direction (that is the rotation direction around the z-axis 4). The activation of the focus positions ensues by a deflection of an electron beam that forms the focal spot with a magnetic field produced by one or more electromagnets (not shown) in the x-ray tube 2. The deflection of the electron beam is linear relative to the current of the magnetic deflection system, at least over a limited region.

A multi-line detector 3 is located opposite the x-ray tube 2. The multi-line detector 3 is moved together with the x-ray tube 2 in an orbital manner around the z-axis (which here also corresponds to the system axis 4). The radiation emanating from the x-ray tube 2 is thereby measured with regard to its absorption upon passing through a subject lying in the beam path. Here a patient 7 who is movably arranged on a bed 6 in the direction of the system axis 4 is shown as a subject. A scanning of the entire patient 7 or a part of the patient 7 ensues in a known manner.

The control of the entire system ensues via the data/control line 10 from a calculation and control unit 9, which also evaluates the acquired detector output data using integrated programs $Prg_x$. In particular the control of the focus position and the integration timing of the detector data are implemented.

Given a stationary focus, generally a quarter offset of the detector is used to improve the scanning resolution of the detector system. Given such a quarter offset, the detector elements 4 are displaced by a quarter of the detector width in the azimuthal direction relative to the center ray of the x-ray tube through the system axis. As is shown in FIGS. 2 and 3, two different scanning rays 12.1.1 and 12.1.2 result that emanate from a positionally-fixed focus 2.1 on the anode surface 11 given a focus/detector system offset by 180°. Given a complete revolution of a focus/detector system, oppositely-placed scans can easily be offset with regard to their scanning rays such that a redundant scanning can be avoided and each half-revolution of a full revolution supplies new scan information.

A section of a virtual detector element 3.n in the rotation center with spatial distribution of the rays from the oppositely-situated projection directions is shown in FIG. 4. As can be seen, an offset by ¼ of the detector element width viewed from the center line M of the detector element respectively results for both rays generated from opposite positions of the focus.

Given such a sampling, the absorption data are integrated over a plurality of small angle increments, and the respective average value of the angle increment is viewed as the ideal angle of the respective projection.

Figure 12:
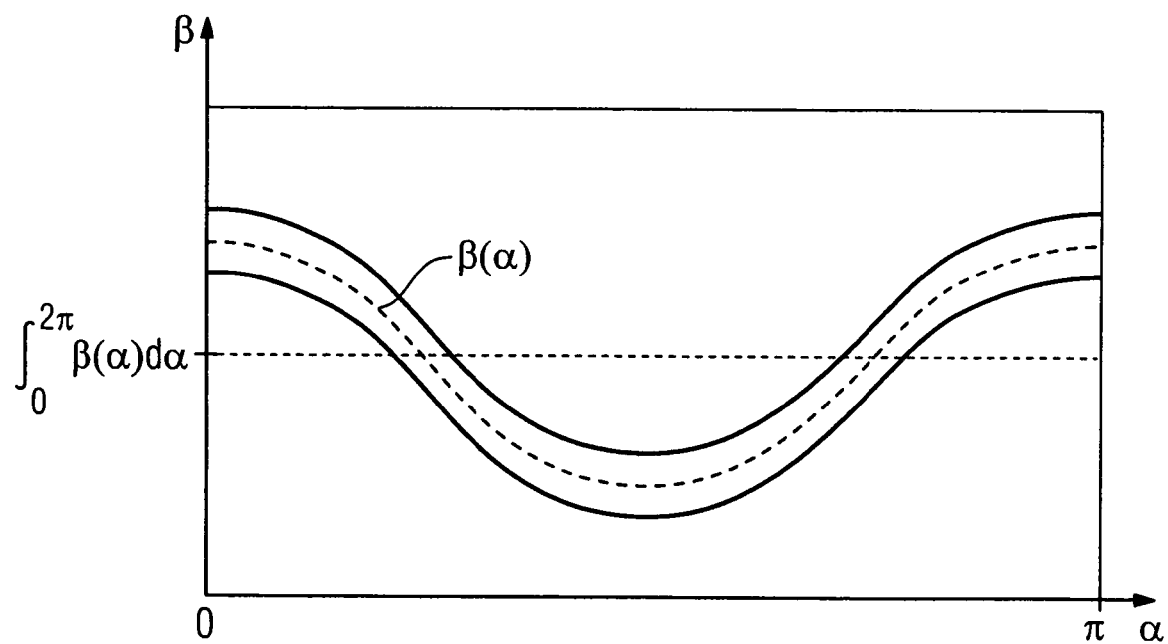
FIG. 12 is a track of an eccentrically-situated mass point in the sinogram of a CT apparatus.

If an eccentrically-situated, optimally punctiform absorber 13 (exemplarily shown in FIGS. 5 and 6) is irradiated in such a one-focus system and a sinogram is acquired as shown in FIG. 12, the position of the focus can be calculated from the sinogram data and the absorption curve according to $$\int_0^{2\pi} \beta(\alpha) d\alpha = 2\pi\Theta,$$

wherein $\alpha$ is the projection angle, $\beta$ is the radiation angle through the absorber and $\Theta$ is the alignment (deflection of the focus in radian measure). In the representation of the sinogram, the dashed center line $\beta(\alpha)$ represents the emphasis line of the curve of the absorptions (dependent on the absorber) on the sinogram, indicated by the solid oscillating lines.

The use of a springing focus with two focus positions in the azimuthal direction is shown in FIGS. 5 and 6 in respective acquisition positions offset by 180°. Four different scan rays 12.1.1, 12.1.2, 12.2.1 and 12.2.2 with different projection angles result, due to the offset of the focus in a detector system with ⅛ offset per detector element 3.n. A precise matching of the integration timing of the detector with the springing frequency of the focus and a precise position of the focus is necessary.

Also shown in FIG. 7 is a section of the virtual detector element in the rotation center with the spatial distribution of the rays 12.x.y from opposite projection directions and from two different focus positions in the azimuthal or $\phi$-direction, corresponding to FIGS. 5 and 6.

If a springing focus with four different positions (as is shown in FIGS. 8 and 9, wherein the focus jumps both in the azimuthal direction and in the z-axis direction) is used, the number of scan rays 12.x.y is doubled relative to that in FIGS. 5 and 6.

An overview of a virtual detector element 3.n in the rotation center is shown in FIG. 10 with spatial distribution of the x-rays from opposite projection directions and each emanating from two different focus positions in the azimuthal direction and in the z-direction is shown in FIG. 10. For better representation of the additional z-offset of the rays, in the overview the arrows shown with the symbol+ represent those directed into the plane of the drawing and the arrows shown with the symbol·represent those directed out of the plane of the drawing.

With regard to FIGS. 2-10, it should be noted that these only schematically show the sample situation for various focus and springing focus arrangements. The scanning actually ensues during the rotation of the focus/detector system and simultaneous integration of detector signals over a number of small angle segments, with the emphasis line of these (spatial) angle segments being considered for simplicity as a scan ray.

Figure 11:
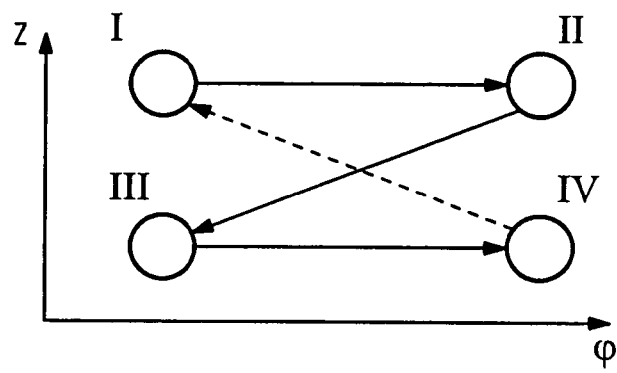
FIG. 11 shows an example of a jump sequence of four focus positions.

An example of a jump sequence of the focus positions is shown in FIG. 11. Here four focus positions I-IV are designated according to the order of their jump. Initially two azimuthally-differing positions I and II at a z-position are jumped to; both the z-position and the azimuthal position are subsequently changed from II to III in order to subsequently change only the azimuthal coordinate from III to IV again. I is subsequently returned to again by varying both the z-position and the azimuthal position.

Figure 13:
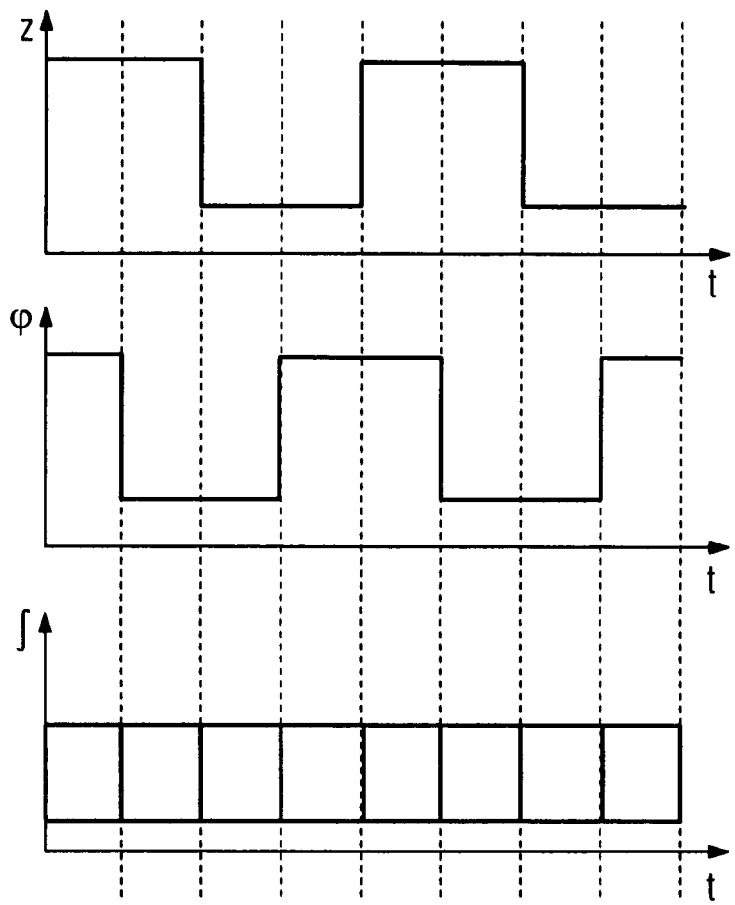
FIG. 13 shows an offset time pattern (raster) of the focus-Z jump, the focus-ϕ jump and the integration time of the detector of a springing focus according to FIG. 8.

Shown in an overview in FIG. 13, from top to bottom, is the offset time pattern of the focus-Z jump z, the focus-$\phi$ jump $\phi$ and the integration timing of the detector of a springing focus according to FIG. 8, respectively plotted relative to the time axis and shown phase-accurately relative to one another.

Due to the ever-finer division of the scan rays, the correct alignment of the springing focus positions is very significantly paired with simultaneously correct integration timing (thus the adjustment of the correct phase relationship between position change and integration behavior), and a simple and correct variant of the adjustment of the correct integration timing and the correct alignment of the springing focus should be achieved. In particular an iterative method of the alignment of the focus positions given an increasing plurality of the focus positions is disproportionally complicated.

According to the invention, a number of measurements with a parameterization according to the following table is implemented to determine and adjust the focus positions and the phase between the springing focus. Three measurements are required in the case of a springing focus with position change in only one coordinate and five measurements are required given a position change in two coordinates.

TABLE 1

| Measurement | 1 | K | N |
|---|---|---|---|
| Phase $\tau$ | $\tau_1 (0 \leq \tau_1 \leq 1)$ | $\tau_1 + k/(2N)$ | $\tau_1 + \frac{1}{2}$ |
| Amplitude $\rho$ | $\rho_1$ | $\rho_k$ | $\rho_N$ |
| Offset $\eta$ | $\eta_1$ | $\eta_1$ | $\eta_1$ |

It should be noted that the offset must be determined given an adjustment of the focus in the azimuthal direction while the offset has no relevance given the adjustment in the system axis direction.

The focus phase $\tau$ is specified in units of the detector integration time. The amplitude values $\rho$ are thereby to be selected differently and can, for example, be distributed, for example, in an equidistant manner in the dynamic range of the deflection current for the focus deflection. The offset $\eta$ represents the deviation of the emphasis of the focus positions from the desired emphasis.

In the following, the evaluation of the N measurements is explained in an example of an azimuthal springing focus. The focus alignment $\Theta_g$ and $\Theta_u$ of the even and odd projections can be determined from each measurement. The difference of the focus alignment values is obtained as a function of the parameters $\tau$ and $\rho$. Under the assumption of a linear correlation, sections of $\Theta(\tau, \rho)$ can be determined by scaling for $\rho$=constant, according to:

$$(\Theta_1 - \Theta_2)(\tau_i, \rho_k) = (\Theta_1 - \Theta_2)(\tau_i, \rho_i) \cdot \frac{\rho_k}{\rho_i}, \text{ with } 1 \leq k, i \leq N$$

The phase $\tau_i$ belonging to the maximum can be determined via interpolation for each $\rho_k$. The optimal phase then results as an average value:

$$\tau^{opt} = 1/N \cdot \sum_{k=1}^{N} \tau_k^*$$

The optimal deflection amplitude is achieved given a springing focus with two positions for $(\Theta_g - \Theta_u)(\tau^*_k, \rho^{opt}) = 0.5$. The corresponding value can be determined via interpolation of the function $(\Theta_g - \Theta_u)(\tau^*_k, \rho)$.

For example, the focus offset $\Theta^{int}$ that is associated with the offset deflection on the anode plate $\eta_1$ can now be determined from the two measurements with $\tau_1$ and $\tau_1 + \frac{1}{2}$ with the following equation:

$$\Theta_{u,g}^{int} = \frac{1}{1 + \frac{\rho(\tau_1)}{\rho(\tau_1 + 1/2)}} \cdot \left( \Theta_{u,g}(\tau_1) + \frac{\rho(\tau_1)}{\rho(\tau_1 + 1/2)} \Theta_{u,g}(\tau_1 + 1/2) \right)$$

The offset value $\Theta^{int}$ is calculated as an average value of $\Theta_u^{int}$ and $\Theta_g^{int}$. If the optimal offset value $\Theta^{opt}$ is intended, for example for a ⅛ offset, the focus deflection $\eta^{opt}$ required for this results at the anode plate from the x-ray set:

$$\eta^{opt} = \eta_1 - (\Theta^{int} - \Theta^{opt}) \cdot S \cdot \frac{R_f}{R_d}$$

wherein $R_f$ designates the focus-rotation center distance (spacing) and $R_d$ thereby represents the rotation center-detector distance. S designates the physical size of a detector channel in the rotation center.

The optimal phase and optimal amplitude of a Z-springing focus can be determined in a similar manner. In this case, the offset determination has no significance for the image reconstruction. $\Theta_g - \Theta_u$ is determined in measurements with the spherical phantom by calculation of the difference of the corresponding z-emphasis coordinate in the sinogram.

Figure 14:
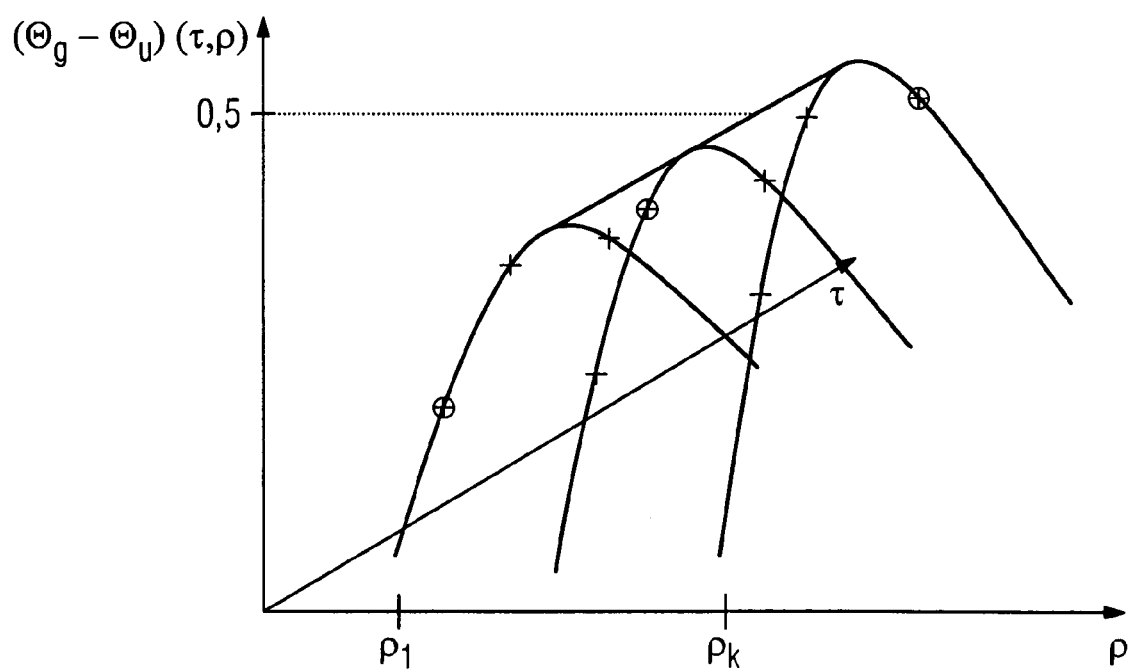
FIG. 14 shows the measurement and extrapolation values for focus adjustment in accordance with the invention.

FIG. 14 illustrates this calculation. A mass point is thus eccentrically introduced into the measurement region of the focus/detector system and the phase shift $\tau$ between the integration frequency of the detector system and the focus springing frequency is established given different values for the deflection current $\rho$ (which is viewed as proportional to the focus deflection). The measurement data are thereby divided such that a sinogram per parameter set is created for each focus position The alignment values $\Theta$ are calculated from these sinograms with the formula $$\int_0^{2\pi} \beta(\alpha) d\alpha = 2\pi\Theta$$

and the differences $\Theta_g - \Theta_u$ for different focus position are determined per parameter set at a coordinate. The indices g and u designate the two different positions.

The difference values $(\Theta_g - \Theta_u)(\tau_i, \rho_k)$ so acquired can be expanded via linear scaling given constant phase or constant deflection current for further difference values for different deflection currents or phases with the equation $$(\Theta_1 - \Theta_2)(\tau_i, \rho_k) = (\Theta_1 - \Theta_2)(\tau_i, \rho_i) \cdot \frac{\rho_k}{\rho_i}$$

Since the difference values $(\Theta_g - \Theta_u)(\tau_i, \rho_k)$ proceed approximately parabolically in the three-dimensional coordinate set according to FIG. 11, a parabolic function with constant deflection current $\rho$ (stated more precisely, the amplitude of the temporally-changing deflection current) can be respectively calculated for this curve from three value sets, and the maximum can therewith be determined. This parabola then essentially corresponds to the curve of the difference values $\Theta_g - \Theta_u$ given constant phase $\tau$. Since the difference value $\Theta_g - \Theta_u$ here exhibits the highest value by definition, the phase $\tau$ is also optimally situated. In principle, the curve can also be approximated via other functions, for example a quadratic function. Naturally it is thereby advantageous when more than three measurement or interpolation values exist, such that possibly-present measurement errors are thereby compensated.

If this maximum of the function for different values of the deflection current $\rho$ is now calculated, the curve of the maximum values can be determined and the deflection current can be determined whose function curve at maximum yields a value of 0.5. Given a springing focus with two focus positions, the optimal deflection current and therewith the optimal deflection are found.

If the measurement for a springing focus should be implemented in the azimuthal direction and system axis direction with 4 positions (as shown in FIG. 11), the phase $\tau$, the amplitude $\rho$ and the offset $\eta$ can initially be determined at a first z-position via adjustment in the azimuthal direction. The z-amplitude of the springing focus can subsequently be determined given a maximal value of 0.5. Finally, the amplitude $\rho$ and the offset $\eta$ are determined at the desired deflection of the springing focus in the z-direction at a second z-position given an already-determined phase $\tau$.

Such a curve of the desired parabolas, thus of the difference values $\Theta_g - \Theta_u$ in units of the width of a detector element as a function of phase $\tau$ and deflection current $\rho$, is shown in FIG. 14. The circled crosses designate measured values; the positions marked with simple crosses designate the values that are determined via scaling of values calculated with the respective ratios of the deflection currents.

If the correct phase $\tau$ is calculated using at least three measurements, the optimal deflection in the other coordinate direction can be calculated in a manner analogous to this with two further measurements, in that the difference of the z-emphases of the spherical phantom is determined at the value 0.5 with the correct phase by interpolation.

If the correct values for the phase and the deflection currents are known from the calculation shown above, these optimal values can be directly set without further iteration steps.

It is understood that the features of the invention described above are usable not only in the specified combination but also in other combinations or alone without departing from the scope of the invention.

Overall, a method for non-iterative focus adjustment in a CT is described with, wherein with a minimal plurality of sinogram acquisitions the position of the center ray is calculated with regard to the movement direction of the focus and the correct phase between the detector sampling frequency and the focus springing frequency is calculated and is adjusted corresponding to predetermined values without iterative steps.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for non-iterative focus adjustment in a computed tomography apparatus comprising at least one x-ray tube with a springing focus on an anode of the x-ray tube, said springing focus changing position on the anode in one dimension at a focus springing frequency, said x-ray tube being rotatable around a system axis, and a multi-line detector disposed opposite said x-ray tube to detect x-ray radiation therefrom, said multi-line detector comprising a plurality of detector elements each operating with a detector sampling frequency equal to said focus springing frequency, said method comprising the steps of:

placing a spherical x-ray absorber in a path of x-rays emitted by said x-ray tube and acquiring at least three sinograms of said spherical absorber with said multi-line detector while said focus is alternating positions in said one dimension on said anode, with different parameters for said respective positions and with different phases between said detector sampling frequency and said focus springing frequency; and from said at least three sinograms, automatically electronically calculating a position of a center ray of said x-ray radiation emitted by said x-ray tube dependent on a movement direction of the focus, and from said position automatically electronically determining the phase between the detector sampling frequency and the focus springing frequency and adjusting said phase based on said position of said center ray dependent on said movement of said focus, to provide an adjusted computer tomography apparatus.

2. A method as claimed in claim 1 comprising generating one of said at least three sinograms for each parameter for each focus position;

automatically electronically calculating an alignment value $\theta$ from said at least three sinograms;

for each parameter, automatically electronically determining differences between the respective alignment values for different focus positions with regard to a coordinate; and extrapolating said difference values by linear scaling with at least one of a constant phase or constant focus position, for further difference values for further different focus positions and phases.

3. A method as claimed in claim 1 comprising scaling said alignment values according to $$(\Theta_1 - \Theta_2)(\tau_i, \rho_k) = (\Theta_1 - \Theta_2)(\tau_i, \rho_i) \cdot \frac{\rho_k}{\rho_i}, \text{ with } 1 \le k, i \le N,$$

wherein $\Theta_1$ and $\Theta_2$ are respective alignments of first and second focus positions, $\tau_i$ is the phase between detector sampling frequency and the focus springing frequency $\rho_k$ and $\rho_i$ are proportional values corresponding to a deflection current used to produce the first and second focus positions, $\Theta_1$ and $\Theta_2$ are alignment calculated from the sinograms of the respective focus position according to $$\int_0^{2\pi} \beta(\alpha) d\alpha = 2\pi\Theta,$$

wherein $\beta(\alpha)$ is the emphasis line of the absorption of the spherical absorber in the sinogram and $\alpha$ is the projection angle.

4. A method as claimed in claim 3 comprising adjusting the focus position and the phase between the detector sampling frequency and the focus springing frequency to produce an equidistant oversampling of detector channels in which said detector elements are disposed.

5. A method as claimed in claim 3 comprising determining the focus position and the phase between the detector sampling frequency and the focus springing frequency by interpolation of $(\Theta_g - \Theta_u)(\tau_i, \rho_k)$, wherein $(\Theta_g - \Theta_u)$ is said difference of said alignment values for different focus positions.

6. A method as claimed in claim 1 comprising adjusting said phase based on said position of said center ray dependent on said movement of said focus non-iteratively and corresponding to predetermined values.

7. A method as claimed in claim 1 comprising using said adjusted computed tomography apparatus to irradiate a subject with said x-ray tube and detect x-ray radiation, attenuated by the subject, as image data using said multi-line detector, and reconstructing an image of the subject from said image data.

8. A method for non-iterative focus adjustment in a computed tomography apparatus comprising at least one x-ray tube with a springing focus on an anode of the x-ray tube, said springing focus changing position on the anode in two dimensions at a focus springing frequency, said x-ray tube being rotatable around a system axis, and a multi-line detector disposed opposite said x-ray tube to detect x-ray radiation therefrom, said multi-line detector comprising a plurality of detector elements each operating with a detector sampling frequency equal to said focus springing frequency, said method comprising the steps of:

placing a spherical x-ray absorber in a path of x-rays emitted by said x-ray tube and acquiring at least five sinograms of said spherical absorber with said multi-line detector while said focus is alternating positions in said two dimensions on said anode, with different parameters for said respective positions and with different phases between said detector sampling frequency and said focus springing frequency; and from said at least five sinograms, automatically electronically calculating a position of a center ray of said x-ray radiation emitted by said x-ray tube dependent on a movement direction of the focus, and from said position automatically electronically determining the phase between the detector sampling frequency and the focus springing frequency and adjusting said phase based on said position of said center ray dependent on said movement of said focus, to provide an adjusted computer tomography apparatus.

9. A method as claimed in claim 8 comprising generating one of said at least five sinograms for each parameter for each focus position;

automatically electronically calculating an alignment value $\theta$ from said at least five sinograms;

for each parameter, automatically electronically determining differences between the respective alignment values for different focus positions with regard to a coordinate; and extrapolating said difference values by linear scaling with at least one of a constant phase or constant focus position, for further difference values for further different focus positions and phases.

10. A method as claimed in claim 9 comprising scaling said alignment values according to $$(\Theta_1 - \Theta_2)(\tau_i, \rho_k) = (\Theta_1 - \Theta_2)(\tau_i, \rho_i) \cdot \frac{\rho_k}{\rho_i}, \text{ with } 1 \leq k, i \leq N,$$

wherein $\Theta_1$ and $\Theta_2$ are respective alignments of first and second focus positions, $\tau_i$ is the phase between detector sampling frequency and the focus springing frequency $\rho_k$ and $\rho_i$ are proportional values corresponding to a deflection current used to produce the first and second focus positions, $\Theta_1$ and $\Theta_2$ are alignment calculated from the sinograms of the respective focus position according to $$\int_0^{2\pi} \beta(\alpha) d\alpha = 2\pi\Theta,$$

wherein $\beta(\alpha)$ is the emphasis line of the absorption of the spherical absorber in the sinogram and $\alpha$ is the projection angle.

11. A method as claimed in claim 10 comprising adjusting the focus position and the phase between the detector sampling frequency and the focus springing frequency to produce an equidistant oversampling of detector channels in which said detector elements are disposed.

12. A method as claimed in claim 10 comprising determining the focus position and the phase between the detector sampling frequency and the focus springing frequency by interpolation of $(\Theta_g - \Theta_u)(\tau_i, \rho_k)$, wherein $(\theta_g - \theta_u)$ is said difference of said alignment values for different focus positions.

13. A method as claimed in claim 8 comprising adjusting said phase based on said position of said center ray dependent on said movement of said focus non-iteratively and corresponding to predetermined values.

14. A method as claimed in claim 8 comprising using said adjusted computed tomography apparatus to irradiate a subject with said x-ray tube and detect x-ray radiation, attenuated by the subject, as image data using said multi-tine detector, and reconstructing an image of the subject from said image data.

* * * * *